United States Patent [19]

Endo et al.

[11] Patent Number: 5,417,981
[45] Date of Patent: May 23, 1995

[54] THERMOPLASTIC POLYMER COMPOSITION AND MEDICAL DEVICES MADE OF THE SAME

[75] Inventors: Fumiaki Endo, Fuji; Nobuko Saiga, Hadano, both of Japan

[73] Assignee: Terumo Kabushiki Kaisha, Tokyo, Japan

[21] Appl. No.: 53,499

[22] Filed: Apr. 28, 1993

[30] Foreign Application Priority Data

Apr. 28, 1992 [JP] Japan .................................. 4-136329

[51] Int. Cl.⁶ .......................... A61K 9/00; A61F 2/06; A61M 25/00
[52] U.S. Cl. .................................... 424/486; 424/422; 424/423; 424/487; 514/772.3; 514/772.7; 523/112; 604/265; 623/1
[58] Field of Search ............... 424/78.17, 78.36, 78.37, 424/422, 486, 487, 423; 514/772.1, 772.3, 772.7; 523/112; 604/265; 606/264, 266; 623/1

[56] References Cited

U.S. PATENT DOCUMENTS

| | | | |
|---|---|---|---|
| 3,625,745 | 12/1971 | Wright et al. | 117/93.31 |
| 4,243,776 | 6/1981 | Marconi et al. | 525/420 |
| 4,353,996 | 10/1982 | Marconi et al. | 523/105 |
| 5,030,448 | 7/1991 | Hunter | 424/83 |
| 5,071,649 | 12/1991 | Hunter | 424/78.38 |
| 5,302,393 | 4/1994 | Matsumoto et al. | 424/423 |

FOREIGN PATENT DOCUMENTS

| | | |
|---|---|---|
| 0523555A1 | 1/1993 | European Pat. Off. . |
| 2142277 | 1/1973 | France . |
| 2399836 | 3/1979 | France . |
| 2812174 | 7/1978 | Germany . |

OTHER PUBLICATIONS

The Merck Index, Eleventh Edition, Editor Susan Budavari, Nov. 1989, p. 529.

P. Jacobs and Elaine Knottenbelt, "The antithrombic drugs in clinical practice," S. Afr. Medical Journal, vol. 63, No. 26, Jun. 25, 1983, pp. 997–1006.

Walter Marconi, New Nonthrombogeenic Polymer Compositions, Makromolekulare Chemie., vol. 5, Apr. 1981, pp. 15–29.

Database WPIL, Week 9038, Derwent Publications Ltd.

*Primary Examiner*—John Kight, III
*Assistant Examiner*—Shelley A. Dodson
*Attorney, Agent, or Firm*—Burns, Doane, Swecker & Mathis

[57] ABSTRACT

A thermoplastic polymer composition containing a protease inhibiting substance and medical devices entirely or partly made of the thermoplastic polymer composition.

Various medical devices having a good compatibility with blood can be made easily by melt-molding the thermoplastic polymer composition. The anti-thrombotic property of the medical devices lasts for a longer time because the protease inhibiting substance exudes out to the surface if rubbed off.

24 Claims, No Drawings

THERMOPLASTIC POLYMER COMPOSITION AND MEDICAL DEVICES MADE OF THE SAME

BACKGROUND OF THE INVENTION

This invention relates to a thermoplastic polymer composition having a good compatibility with blood and to medical devices made of the thermoplastic polymer composition.

Research and development to equip medical devices with an anti-thrombotic property have become active recently. The method used for equipping medical devices with an anti-thrombotic property is to coat the surfaces (particularly the parts of them which contact with blood) of medical devices made of synthetic resins with anti-thrombotic substances. The anti-thrombotic substances used are fibrinolytic substances (urokinase, streptokinase, etc.), anti-thrombogenic substances (polysaccharides, prostaglandin, etc.), and neointima formation accelerating substances. The coating of a protease inhibiting substance is formed by application or chemical bonding (ionic or covalent bond).

The conventional method for equipping medical devices with an anti-thrombotic property thus needs a separate process for applying or chemically binding a protease inhibiting substance to the surfaces of the medical devices formed in the prior process, which requires a high level of technology according to the medical devices manufactured, the substances used, and other conditions.

In addition, the formation by application has the problems of an unsatisfactory durability of the coating and changes in the dimensions of medical devices (increase of the external diameter and decrease of the internal diameter) caused by the coating. It often needs an appropriate binder and also needs a solvent for dissolving or dispersing the protease inhibiting substance and binder to apply. The residual binder and solvent must be removed from the coating formed.

The formation by chemical bonding, on the other hand, needs a complicated process to introduce ionic groups or groups with a covalent bond forming ability into both the surface of the medical device and the protease inhibiting substance. Further, the group-introduction process can restrict the kind of material and protease inhibiting substance usable for the medical device to be manufactured. It can deteriorate partly or completely the anti-thrombotic property of the protease inhibiting substance because of the denaturation caused by ionic or covalent bonding. It also increase the cost of the medical device manufactured.

Moreover, it is difficult to form a coating of a protease inhibiting substance over the portions of the surface put in contact with blood of medical devices formed beforehand evenly with no areas left uncovered, particularly when the shapes of the medical devices are very complicated.

The object of this invention is to provide a novel thermoplastic polymer composition which can provide the entire body of medical devices with a compatibility with blood, especially an anti-thrombotic property, and medical devices made of the thermoplastic polymer composition.

SUMMARY OF THE COMPOSITION

A thermoplastic polymer composition of this invention comprises a thermoplastic polymer and a protease inhibiting substance.

A medical device of this invention are entirely or partly made of the thermoplastic polymer composition of this invention.

DETAILED DESCRIPTION OF THE PREFERRED EMBODIMENTS

A thermoplastic polymer composition of this invention comprises a thermoplastic polymer as the main constituent and a protease inhibiting substance added to the thermoplastic polymer.

The protease inhibiting substance used for the thermoplastic polymer composition of this invention acts on at least one of the 13 blood coagulation factor precursors (fibrinogen, prothrombin, tissue thromboplastin, plasma thromboplastin, prekallikrein, for example) and activated coagulation factors formed from those precursors (thrombin, plasmin, kallikrein, etc.) and inhibits its activity to prevent or repress the coagulation of blood. In short, the protease inhibiting substance inhibits the activity of the humoral factors of the coagulation system in blood.

The protease inhibiting substance is preferably a synthetic substance. The molecular weight is preferably about 200 to about 3000. The melting point is preferably 80° to 300° C. The substance stable while melted is preferable. A decomposition point of the protease inhibiting substance is preferably higher than a melting point of the thermoplastic polymer and about 90° C. or higher.

Specifically, synthetic protease inhibiting substances usable for this invention include gabexate mesylate (mesyl is abbreviated name of methane-sulfonic acid) [ethyl-4-(6-guanidino-hexanoyloxy) benzoate methanesulfonate], naphamostat mesylate [6-amidino-2-naphthy-p-guanidinobenzoate dimethanesulfonate], benzamidine-hydrochloride, dipyridamole [2,6-bis(diethanolamino)-4,8-dipiperidinylpyrimido(5,4-d) pyrimidine], and trapidil [7-diethylamino-5-methyl-s-triazolo(1,5-a)pyrimidine], for example.

The above protease inhibiting substances, unlike conventional mucopolysaccharide such as heparin, have a high heat resistance as well as a high protease inhibiting activity.

Preferable synthetic protease inhibiting substances have an amidino group shown by formula [I] below or that ionized positively shown by formula [III], or a guanidino group shown by formula [II] below or that ionized positively shown by formula [IV] as their functional group.

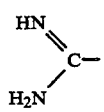

[I]

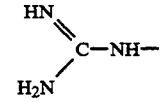

[II]

-continued

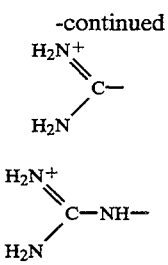

Gabexate mesylate has a structure shown by formula [V] and has with one guanidino group. Naphamostat mesylate has a structure shown by formula [VI] and has one amidino group and one guanidino group. Benzamidinehydrochloride has a structure shown by formula [VII] and has one amidino group.

Of these protease inhibiting substances, naphamostat mesylate has a very high heat resistance (decomposition point of about 260° C.) and therefore can be added to various thermoplastic polymers. In addition, naphamostat mesylate has also a preferable high protease inhibiting activity.

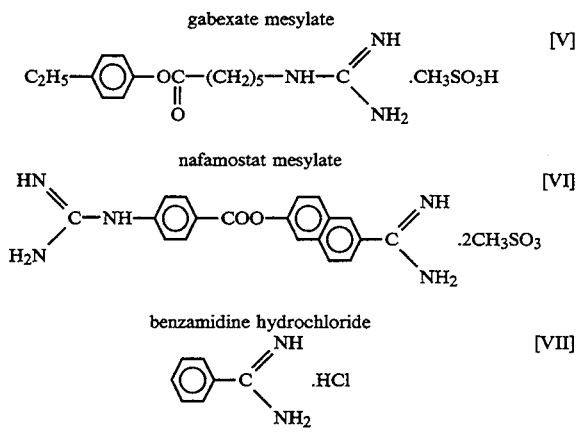

The protease inhibiting substance for this invention has preferably a higher heat resistance (decomposition temperature) than the thermoplastic polymer used and a good solubility in the thermoplastic polymer. It is also preferable that the protease inhibiting substance added to the thermoplastic polymer dissolves from the surface of medical devices into blood gradually by an amount effective to prevent or repress the coagulation of blood.

The protease inhibiting substance for this invention must not lose the protease inhibiting activity by the molding temperature of the thermoplastic polymer used in the manufacturing process of medical devices.

The protease inhibiting substance used may be a simple substance or a mixture of two or more substances if they do not exert a bad influence upon each other.

For the thermoplastic polymer as the main constituent of the thermoplastic polymer composition of this invention, any melt-moldable polymer can be used. Specifically, polymers usable for this invention include polyester, polyamide, thermoplastic polyurethane, homopolymer and copolymer of olefins (polyethylene, polypropylene, ethylene-propylene copolymer, ethylene-propylene-diene trimer, ethylene-vinyl acetate copolymer, ethylene-vinyl alcohol copolymer, ethylene-vinyl chloride copolymer, etc.), homopolymer and copolymer of methacrylic acid esters, homopolymer and copolymer of vinyl chloride, poly(vinyl acetate), styrene-butadiene copolymer, acrylonitrile-butadiene copolymer, natural rubber, synthetic rubber (isoprene rubber, butadiene rubber, chloroprene rubber, isobutylene-isoprene rubber), and silicone rubber.

The thermoplastic polymer for this invention may be a simple polymer or a mixture of two or more polymers. One or more polymers most suited for the use and structure of the medical device fabricated can be selected from the usable thermoplastic polymers described above.

Thermoplastic polymers having a melt-molding temperature lower than the resisting temperature (decomposition temperature) of the protease inhibiting substance used and a large dissolving capacity for the protease inhibiting substance (a strong affinity for the protease inhibiting substance) are preferable for the thermoplastic polymer of this invention.

Further, thermoplastic polymers with a microdomain structure (micro phases separation structure) are preferable for the thermoplastic polymer of this invention. The microdomain configuration may be lamellar, insular or cylindrical. The microdomain structure may be formed by crystal and non-crystal phases or hydrophilic and hydrophobic phases. A microdomain structure formed by crystal and non-crystal phases is preferable for this invention.

Thermoplastic polymers with a microdomain structure have a good antiplatelet property and consequently some extent of anti-thrombotic property themselves. However, their inhibiting activity on the humoral factors of the coagulation system in blood is considered to be unsatisfactory. Therefore, this invention adds an appropriate protease inhibiting substance to a thermoplastic polymer with a microdomain structure to provide the thermoplastic polymer with an increased inhibiting action on the humoral factors of the coagulation system in blood in addition to their good antiplatelet property.

There are various thermoplastic polymers with a microdomain structure, but those having polyether chains such as polypropylene oxide chains, polyethylene oxide chains, and polytetramethylene oxide chains in their molecules are preferable. Specifically, preferable thermoplastic polymers include polyether polyurethane, polyether polyamide, and polyether polyester. The type of polymerization may be graft copolymerization or block copolymerization, but the block copolymerization is preferable. The block copolymerization has an An-Bn type, an An-Bn-An type and a (A-B) n type. The (A-B) n type is preferable.

By using these thermoplastic polymers having polyether chains in their molecules, the thermoplastic polymer composition of this invention has a slower releasing capability for the protease inhibiting substance caught in it. The medical devices made of the thermoplastic polymer composition then retain the anti-thrombotic property for a longer time. The protease inhibiting substance added to thermoplastic polymers with polyether chains in their molecules is considered to be dissolved and caught by the polyether chain portions of the polymer and gradually released outside along the polyether chain portions.

The amount of the protease inhibiting substance added to the thermoplastic polymer is determined by many conditions such as the shape and use of the medical device manufactured, the size of the surface of the medical device which comes into contact with blood, the type of thermoplastic polymer used for the medical device, the protease inhibiting activity of the protease inhibiting substance used, and the exudation rate of the protease inhibiting substance from the thermoplastic polymer. The amount of the protease inhibiting substance is generally about 100 ppm to about 25 wt % of that of the thermoplastic polymer and preferably 500 ppm to 20 wt %.

The thermoplastic polymer composition of this invention may be unshaped mixture or shaped into pellets, sheets or rods by melt-kneading or extrusion of the mixture.

Further, the thermoplastic polymer composition of this invention may also contain various additives used for thermoplastic polymers unless they deteriorates the compatibility with blood of the medical devices made of the composition.

The medical devices of this invention are entirely or partly made of the thermoplastic polymer composition of this invention described above. In other words, at least the portions forming the surfaces which contact with blood are made of the composition of this invention. When only the portions forming the surfaces which contact with blood are made of the composition of this invention, the other portions are made by a thermoplastic polymer with no protease inhibiting substance and those portions are connected to complete a medical device.

The medical devices of this invention can be made using the forming methods for conventional thermoplastic polymers, such as extrusion molding, blow molding, extrusion and blow molding, injection molding, injection and blow molding, compression molding, powder molding and casting. Preferable forming methods can be selected according to the thermoplastic polymer composition used and the shape of the medical device.

The thermoplastic polymer composition of this invention can also be formed into various shapes such as tube, film, sheet, plate, fiber, thread, woven cloth, unwoven cloth, rod, syringe, bag, box and tray which can be used as parts of medical devices or medical articles.

The medical devices of this invention include all things used for medical care which have the surfaces put in contact with blood and therefore need the compatibility with blood, particularly anti-thrombotic property, such as artificial organs (artificial kidney, artificial heart, artificial lung, etc.) and their circuit tubes, artificial blood vessel, blood bag, catheter, injection syringe, blood transfusion set and blood filter.

When an excessive-amount of the protease inhibiting substance is present at the surface of a medical device manufactured as described above, it is desired to wash the device and remove the protease inhibiting substance before using the device. This wash may be conducted using water, alcohol or other solvents.

EXAMPLE 1

Naphamostat mesylate (FUTHAN, Torii & Co., Ltd. decomposition point 260° C.) was added 10 wt % to polyether nylon 610 (Terumo Co.) having polypropyrene oxide chains and the crystal and non-crystal microdomain structure. This mixture was melted-kneaded by a double-shaft kneader (LABOPLASTMILL, Toyoseiki Co.) at 240° C. to prepare the thermoplastic polymer composition of this invention (Example 1).

Tubes, 1.10 mm in outer diameter and 0.78 mm in inner diameter, were formed of the above thermoplastic polymer composition by an extrusion molding machine. One end of the tubes was worked to make catheters for an example of the medical device of this invention (Example 7).

Catheters of the same size were formed of ethylene/tetrafluoroethylene copolymer (ETFE) for comparison (comparative example 1).

EXAMPLE 2

Naphamostat mesylate (FUTHAN, Torii & Co., Ltd.) was added 12.5 wt % to polyether polyester (HYTREL 4057, Du Pont-Toray Co., Ltd.) having a lamellar microdomain structure. This mixture was melted-kneaded by a double-shaft kneader (LABOPLASTMILL, Toyoseiki Co.) at 185° C. to prepare the thermoplastic polymer composition of this invention (Example 2).

Catheters for another example of the medical device of this invention (example 8) were made of the above thermoplastic polymer composition in the same manner as in example 1.

EXAMPLE 3

Naphamostat mesylate (FUTHAN, Torii & Co., Ltd.) was added 20 wt % to polyether polyamide (PAE 1200, Ube Industries Ltd.) having the crystal and non-crystal microdomain structure. This mixture was melted-kneaded by a double-shaft kneader (LABOPLASTMILL, Toyoseiki Co.) at 175° C. to prepare the thermoplastic polymer composition of this invention (Example 3).

Catheters for another example of the medical device of this invention (example 9) were made of the above thermoplastic polymer composition in the same manner as in example 1.

EXAMPLE 4

Gabexate mesylate (FOY, Ono Pharmaceutical Co., Ltd.) was added 15 wt % to ethylene-acrylic acid ester-maleic anhydride-trimer (BONDINE, Sumitomo Chemical Co. Ltd.) having no microdomain structure. This mixture was melted-kneaded by a double-shaft kneader (LABOPLASTMILL, Toyoseiki Co.) at 90° C. to prepare the thermoplastic polymer composition of this invention (Example 4).

Catheters for another example of the medical device of this invention (example 10) were made of the above thermoplastic polymer composition in the same manner as in example 1.

EXAMPLE 5

Gabexate mesylate (FOY, One Pharmaceutical Co., Ltd.) was added 10 wt % to polyether polyamide (PEBAX 5562, Atochem Co.) having the lamellar microdomain structure. This mixture was melted-kneaded by a double-shaft kneader (LABOPLASTMILL, Toyoseiki Co.) at 130° C. to prepare the thermoplastic polymer composition of this invention (Example 5).

Catheters for another example of the medical device of this invention (example 11) were made of the above thermoplastic polymer composition in the same manner as in example 1.

EXAMPLE 6

Benzamidine hydrochloride (Aldrich Inc.) was added 15 wt % to polyether polyamide (PEBAX 5562, Atochem Co.) having the crystal and non-crystal microdomain structure. This mixture was melted-kneaded by a double-shaft kneader (LABOPLASTMILL, Toyoseiki Co.) at 130° C. to prepare the thermoplastic polymer composition of this invention (Example 6).

Catheters for another example of the medical device of this invention (example 12) were made of the above thermoplastic polymer composition in the same manner as in example 1.

Test 1

The catheters of examples 7 to 12 and comparative example 1 were subjected to the following test.

A catheter of example 7 and that of comparative example 1 were inserted into the right and left common catotic arteries of a Japanese white house rabbit respectively by cutting the arteries, inserting the common carotic arteries of a Japanese white house rabbit respectively by cutting the arteries, inserting the catheters from the slits, then closing the slits. After 24 hours, the rabbit was dosed with heparin of 1000 units×the body weight (kg), and the blood was let out injecting physiological salt solution. Then the portions of the common carotic arteries where the catheters had been put in for 24 hours were cut open and inspected. No thrombus was formed on the inside and outside surfaces of the catheter of example 7, but thrombi were formed at the upstream portion of the catheter of comparative example 1.

Catheters of examples 8 to 12 were also tested in the same manner, and the results were almost the same as that of the above test.

Thus it was confirmed that the catheters of examples 7 to 12, and hence the thermoplastic polymer compositions of examples 1 to 6, have an anti-thrombotic property.

Test 2

Sheets were formed of the thermoplastic polymer compositions of examples 1 to 4 and polypropylene for comparison (comparative example 2). These sheets were cut into 8×8 mm squares to prepare test samples 1 to 5.

Human platelet-rich plasma so diluted that the number of platelets is $10^5/\mu l$ was dripped 200 $\mu l$ on each of the test samples 1 to 5. The test samples 1 to 5 with the human platelet-rich plasma put on were left alone at room temperature for 30 minutes, washed with phosphoric acid buffer solution, then fixed with glutaraldehyde and dry-frozen. The surfaces of the thus prepared test samples 1 to 5 were photographed using a scanning electron microscope at 1000 magnifications. The morphologies of the platelets adhering to the surface of each test sample were classified, and the number of the platelets of each class was counted. The results were as shown in Table I blow.

TABLE I

| Test Sample No. | Morphologies of Adhering Platelets | | |
|---|---|---|---|
| | Type Ia | Type Ib | Type II |
| 1 (Example 1) | 0 | 2 | 1 |
| 2 (Example 2) | 1 | 0 | 1 |
| 3 (Example 3) | 0 | 0 | 3 |
| 4 (Example 4) | 5 | 23 | 461 |
| 5 (Co.Ex. 2) | 3 | 9 | 552 |

Classification of Platelet Morphologies
Type I: Nonactivated Adhesion
Type Ia: Normal discoid Type Ib: Changed into a spherical form but not yet protruded pseudopodia
Type II: Activated Adhesion Adhering with protruded pseudopodia The thermoplastic polymer composition of this invention contains a protease inhibiting substance and hence has an anti-thrombotic property imparted by the protease inhibiting substance. Therefore, it has the following advantages.

Various medical devices having a good compatibility with blood can be made very easily by melt-molding the thermoplastic polymer composition.

The medical devices thus made using the thermoplastic polymer composition of this invention have an anti-thrombotic property all over their surfaces, eliminating the need to coat their surfaces with an protease inhibiting substance and thereby solving the problems with the coating process.

The medical devices of this invention retain the anti-thrombotic property for a much longer time than conventional medical devices, whose anti-thrombotic property is given by the protease inhibiting substance on the surface which can be rubbed off and lost.

The medical devices of this invention can be made accurately according to the designed dimensions, because coating of a protease inhibiting substance after molding, which causes changes in the dimensions, is not required.

The medical devices of this invention do not need a binder for retaining a protease inhibiting substance to their surface nor a solvent for dissolving or dispersing the binder and the protease inhibiting substance for their manufacturing process and hence the process of removing the residual binder and solvent. Therefore, the medical devices of this invention are safer than conventional ones.

The medical devices of this invention do not need the process to introduce ionic groups or groups with a covalent bond forming ability into the surface of the medical device and the protease inhibiting substance, eliminating a possible deterioration of the physical and chemical properties of medical devices.

What is claimed is:

1. A thermoplastic polymer composition comprising a mixture of thermoplastic polymer and a protease inhibiting substance having a decomposition temperature higher than a melting point of the thermoplastic polymer and at least an amidino group, positively ionized amidino group, guanidino group, or positively ionized guanidino group.

2. The thermoplastic polymer composition of claim 1, wherein said protease inhibiting substance is a protease inhibiting substance selected from the group consisting of gabexate mesylate, naphamostat mesylate and benzamidine-hydrochloride.

3. The thermoplastic polymer composition of claim 1, wherein said thermoplastic polymer is a thermoplastic polymer which has a microdomain structure.

4. The thermoplastic polymer composition of claim 1, wherein said thermoplastic polymer is a thermoplastic polymer which contains at least a polyether chain in the molecule.

5. The thermoplastic polymer composition of claim 1, wherein said thermoplastic polymer is a polyether polyurethane block copolymer, polyether-polyamide block copolymer, or polyether-polyester block copolymer.

6. A medical device entirely or partly made of a thermoplastic polymer composition, said thermoplastic polymer composition comprising a mixture of thermoplastic polymer and a protease inhibiting substance having a decomposition temperature higher than a melting point of the thermoplastic polymer and at least an amidino group, positively ionized amidino group, guanidino group, or positively ionized guanidino group.

7. The medical device of claim 6, wherein said protease inhibiting substance is a protease inhibiting substance selected from the group consisting of gabexate mesylate, naphamostat mesylate and benzamidine-hydrochloride.

8. The medical device of claim 6, wherein said thermoplastic polymer is a thermoplastic polymer which has a microdomain structure.

9. The medical device of claim 6, wherein said thermoplastic polymer is a thermoplastic polymer which contains at least a polyether chain in the molecule.

10. The medical device of claim 6, wherein said thermoplastic polymer is a polyether-polyurethane block copolymer, polyether-polyamide block copolymer, or polyether-polyester block copolymer.

11. The medical device of claim 6, wherein said medical device is a catheter.

12. The medical device of claim 6, wherein said medical device is a artificial blood vessel.

13. A method for preparing a thermoplastic polymer composition for making a medical device comprising melt-kneading a thermoplastic polymer composition and a protease inhibiting substance having a decomposition temperature higher than a melting point of the thermoplastic polymer.

14. A method for preparing a thermoplastic polymer composition of claim 13, wherein said protease inhibiting substance is a protease inhibiting substance selected from the group consisting of gabexate mesylate, naphamostat mesylate and benzamidine-hydrochloride.

15. A method for preparing a thermoplastic polymer composition of claim 13, wherein said thermoplastic polymer is a thermoplastic polymer which has a microdomain structure.

16. A method for preparing a thermoplastic polymer composition of claim 13, wherein said thermoplastic polymer is a thermoplastic polymer which contains at least a polyether chain in the molecule.

17. A method for preparing a thermoplastic polymer composition of claim 13, wherein said thermoplastic polymer is a polyether polyurethane block copolymer, polyether-polyamide block copolymer, or polyether-polyester block copolymer.

18. A method for making a medical device comprising mixing a thermoplastic polymer composition with a protease inhibiting substance having a decomposition temperature higher than a melting point of the thermoplastic polymer by melt-kneading to form a mixed composition, and forming said mixed composition into a shape of a medical device.

19. A method for making a medical device of claim 18, wherein said protease inhibiting substance is a protease inhibiting substance selected from the group consisting of gabexate mesylate, naphamostat mesylate and benzamidine-hydrochloride.

20. A method for making a medical device of claim 18, wherein said thermoplastic polymer is a thermoplastic polymer which has a microdomain structure.

21. A method for making a medical device of claim 18, wherein said thermoplastic polymer is a thermoplastic polymer which contains at least a polyether chain in the molecule.

22. A method for making a medical device of claim 18, wherein said thermoplastic polymer is a polyether polyurethane block copolymer, polyether-polyamide block copolymer, or polyether-polyester block copolymer.

23. A method for making a medical device of claim 18, wherein said process of forming into a shape of a medical device is carried by a forming method selected from the group consisting of extrusion molding, blow molding, extrusion and blow molding, injection molding, injection and blow molding, compression molding, powder molding and casting.

24. A method for making a medical device of claim 18, wherein said medical device is an artificial blood vessel or a catheter.

* * * * *

UNITED STATES PATENT AND TRADEMARK OFFICE
CERTIFICATE OF CORRECTION

PATENT NO. : 5,417,981
DATED : May 23, 1995
INVENTOR(S) : Fumiaki ENDO et al

It is certified that error appears in the above-indentified patent and that said Letters Patent is hereby corrected as shown below:

In Column 6, line 52, delete "One" and insert -- Ono --.

In Column 7, line 14, delete "catotic" and insert -- carotic --.

Signed and Sealed this

Twenty-fifth Day of July, 1995

Attest:

BRUCE LEHMAN

*Attesting Officer*  *Commissioner of Patents and Trademarks*